United States Patent
Allen et al.

(10) Patent No.: US 10,190,090 B2
(45) Date of Patent: Jan. 29, 2019

(54) METHODS AND SYSTEMS FOR FORMING STABLE PARTICLES FROM SUSPENDED SOLIDS PRODUCED BY ETHANOL FERMENTATION

(71) Applicant: Water Solutions, Inc., Sioux Falls, SD (US)

(72) Inventors: Stephen D. Allen, Eagle, ID (US); Mike LoCascio, Clear Lake, IA (US)

(73) Assignee: WATER SOLUTIONS, INC., Sioux Falls, SD (US)

( * ) Notice: Subject to any disclaimer, the term of this patent is extended or adjusted under 35 U.S.C. 154(b) by 188 days.

(21) Appl. No.: 15/293,039

(22) Filed: Oct. 13, 2016

(65) Prior Publication Data

US 2017/0152471 A1 Jun. 1, 2017

Related U.S. Application Data

(60) Provisional application No. 62/240,821, filed on Oct. 13, 2015.

(51) Int. Cl.
*C12N 1/16* (2006.01)
*C12P 7/06* (2006.01)

(52) U.S. Cl.
CPC . *C12N 1/16* (2013.01); *C12P 7/06* (2013.01)

(58) Field of Classification Search
CPC ...................................................... C12N 1/16
See application file for complete search history.

(56) References Cited

U.S. PATENT DOCUMENTS

| | | | | |
|---|---|---|---|---|
| 4,226,939 A | * | 10/1980 | Wegner | C12N 1/00 435/247 |
| 4,508,737 A | * | 4/1985 | Forest | A23K 30/15 426/335 |
| 8,067,193 B2 | * | 11/2011 | Hughes | C02F 1/56 426/11 |
| 2006/0006116 A1 | * | 1/2006 | Scheimann | C02F 1/56 210/728 |
| 2010/0178675 A1 | * | 7/2010 | Lawton, Jr. | C07K 14/425 435/71.1 |
| 2012/0125859 A1 | * | 5/2012 | Collins | B01D 17/0217 210/708 |

* cited by examiner

*Primary Examiner* — Peter Keyworth
(74) *Attorney, Agent, or Firm* — Kirton McConkie; Evan R. Witt

(57) ABSTRACT

Methods and systems for forming stable particles from suspended solids produced by ethanol fermentation are disclosed. The methods include providing a fraction from ethanol fermentation containing solids and suspended solids. The pH of the fraction is adjusted, if necessary. A reducing agent is added. A high molecular weight anionic polymer is added to form stable particles of solids and suspended solids. Lastly, the stable particles are free drained to separate them from a treated liquid portion. The treated liquid portion is added as backset to the fermentation process while the recovered solids are further processed into useful products.

13 Claims, 4 Drawing Sheets

METHODS AND SYSTEMS FOR FORMING STABLE PARTICLES FROM SUSPENDED SOLIDS PRODUCED BY ETHANOL FERMENTATION

CROSS-REFERENCE TO RELATED APPLICATIONS

N/A

TECHNICAL FIELD

The present disclosure relates to methods and systems for forming stable particles from suspended solids produced by ethanol fermentation. More specifically, the present disclosure relates to enhancing the formation of stable particles by treating stillage with reducing agents and high molecular weight anionic polymers.

BACKGROUND

Fermentation is a biological process that uses yeasts to convert feedstocks such as grains and cellulosic plant matter into ethanol. Fermentation processes can be used to generate potable ethanol in the form of liquors and other alcoholic beverages as well as to generate industrial or fuel ethanol. Fermentation is often coupled with distillation processes that isolate the ethanol from the fermentation mixture. While the fermentation and distillation processes can effectively generate and isolate ethanol, the remaining liquids and solids can pose a problem for operators of ethanol production facilities. The remaining liquids and solids must either be disposed of or undergo further processing to generate viable commodities. Both disposal and/or processing of these remaining liquids and solids can increase the costs and complexity of ethanol production. For example, while further processing of the remaining liquids can render them suitable to be reused at least in part in the fermentation process, this further processing can be costly and there are limits to the amount of liquid that can be recycled. Likewise, there are increased costs and limitations to further processing the remaining solids into useful products.

In general, in conventional ethanol production, a prepared and/or processed mixture of feedstock is fermented to generate ethanol. An "ethanol" fraction is further processed by distillation to isolate ethanol. The fraction remaining after distillation is known as "whole stillage" and is separated into a more solid fraction known as "wet grains" and a more liquid fraction known as "thin stillage." Wet grains can contain from about 7-17% solids and can be sold as "wet distillers grains" or can be dried to be sold as "dried distillers grains" ("DDG") or "dried distillers grains with solubles" ("DDGS"). While the separation process removes some of the total solids (TS) and total suspended solids (TSS) that are found in the whole stillage, substantial amounts remain in the thin stillage. The thin stillage can also contain unfermented feedstock components such as hemicellulose, yeasts, and other solids typically associated with structural components of the feedstock (e.g., biotins, dextrans, and other similar components). Thin stillage can be recycled as "backset" into the fermentation step to take the place of some of the water that is added to the prepared and/or processed mixture of feedstock. However, the ratio of thin stillage that can be used as backset is limited in part because of the TS, TSS, solids, and unfermentable components found in the thin stillage. Thin stillage that is not used as backset needs to be further processed by a relatively costly evaporation process to separate water from any remaining solids.

The majority of water that makes up the recipe/mix for a new fermentation (cooking) batch is made up of 1) evaporation condensate (majority); 2) $CO_2$ scrubber water (smallest amount); and 3) backset. If an ethanol fermentation plant had enough evaporation capacity it would send nearly all evaporation condensate back to begin the cooking process. But since ethanol fermentation plants do not have sufficient evaporation capacity, primarily because the evaporation process is very expensive, ethanol fermentation plants return a fraction of the thin stillage untreated as "backset" to the fermentation (cook) process. The percentage of backset that can be used is limited for the reasons listed.

Therefore, although conventional ethanol production provides some processes to recycle the liquids and solids remaining after the fermentation step, these processes are not without their shortcomings. Some examples of shortcomings include the limited ratio of thin stillage that can be used as backset and the cost of further processing by evaporation. Accordingly, it would be an improvement in the art to augment or even replace current technologies with other techniques.

BRIEF SUMMARY

Methods and systems for forming stable particles from suspended solids produced by ethanol fermentation are disclosed. In some embodiments, the present application discloses methods and systems for forming stable particles from suspended solids produced by ethanol fermentation comprising providing a fraction from ethanol fermentation where the fraction can comprise one or more of solids and suspended solids. The pH of the fraction can be adjusted. A reducing agent is added. A high molecular weight anionic polymer is added to form stable particles of one or more of solids and suspended solids. Lastly, the stable particles from a liquid portion can be free drained to separate them from a liquid portion. The treated liquid portion can be added as backset to the fermentation process while the recovered solids can be further processed into useful products.

The disclosed methods and systems for forming stable particles from suspended solids produced by ethanol fermentation have at least two primary benefits to the ethanol fermentation plant: 1) by removing the TS/TSS from the backset in a cost effective manner it improves the percentage of backset that can be effectively recycled to the initial fermentation (cook) batch; and 2) by increasing the percentage of backset recycled by the plant, the amount of thin stillage going to the evaporators is reduced, which significantly reduces or eliminates the high chemical and operational costs associated with running and maintaining evaporators. In some cases the disclosed methods and systems may be able to eliminate the use of evaporation all together from the ethanol fermentation process.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION OF THE INVENTION

Figure 1:
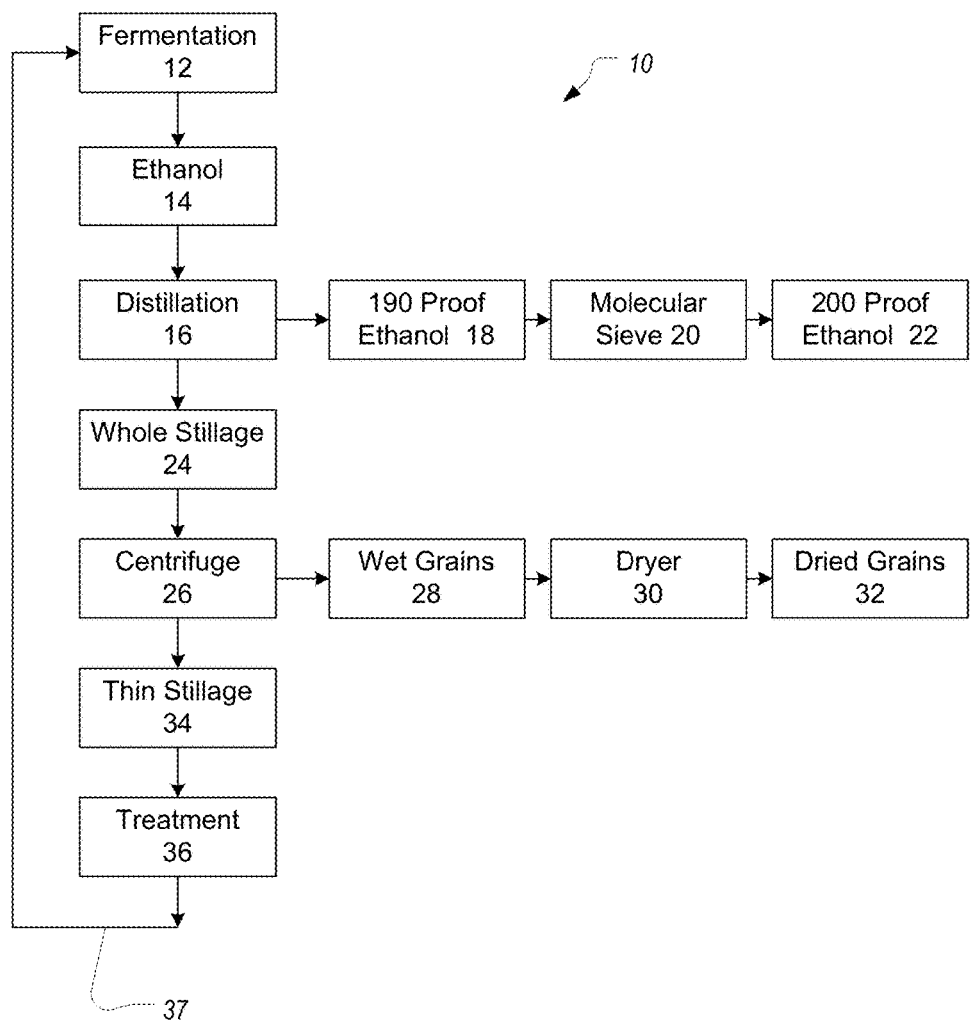
FIG. 1 illustrates methods and systems for treating liquids and solids remaining after fermentation.

In general (and as mentioned above), some embodiments of the described systems and methods relate to forming stable particles from suspended solids produced by ethanol fermentation. While the described methods can comprise any suitable steps or process, FIG. 1 shows that, at least in some embodiments, the described methods comprise a method 10 for forming stable particles from suspended solids produced by ethanol fermentation. In some embodiments, method 10 comprises one or more optional steps including a fermentation step 10, an ethanol step 14, a distillation step 16, a 190 proof ethanol step 18, a molecular sieve step 20, a 200 proof ethanol step 22, a whole stillage step 24, a centrifuge step 26, a wet grains step 28, a dryer step 30, a dried grains step 32, a thin stillage step 34, and/or a treatment step 36.

The fermentation step 10 can include any suitable fermentation process including the fermentation of a suitable feedstock. The ethanol step 14 can comprise the resulting ethanol fraction from the fermentation step, together with the fermented and unfermented feedstock solids. The distillation step 16 can comprise one or more distillation steps to isolate ethanol from the feedstock solids. The 190 proof ethanol step 18 can comprise recovering 190 proof ethanol from the distillation step. The molecular sieve step 20 can comprise any suitable methods or process to dehydrate the 190 proof ethanol. The 200 proof ethanol step 22 can comprise recovering 200 proof ethanol from the molecular sieve step. The whole stillage step 24 can comprise recovering the remaining fraction from the distillation step. The centrifuge step 26 can comprise any suitable mechanical separation process for separating a wet grains fraction from a thin stillage fraction. The wet grains step 28 can comprise recovering wet grains, including fermented and unfermented feedstock solids, from the centrifuge step. The dryer step 30 can comprise any suitable method of drying the wet grains. The dried grains step 32 can comprise any suitable step for recovering the dried grains from the drying step. The thin stillage step 34 can comprise any suitable step for recovering a liquid fraction or thin stillage from the centrifuge step. The treatment step 36 can comprise any suitable method for treating the thin stillage to generate and stabilized particles formed from solids and suspended solids.

In some embodiments, stillage can refer to any fraction produced by fermentation. In other embodiments, whole stillage can refer to what is sometimes known in the industry as slops, thick stillage, beer bottoms, spent mash, and/or spent grains. In yet other embodiments, thin stillage can refer to what is sometimes known in the industry as centrate, back set, set back, evaporator feed, slop, and/or solubles. In some embodiments, wet grains can refer to wet cake and/or wet distillers grains (WDG). In some ethanol fermentation embodiments, vinasse can refer to a fraction remaining after fermentation of sugarcane and/or sugar beet such as cane-vinasse or beet-vinasse.

Figure 2:
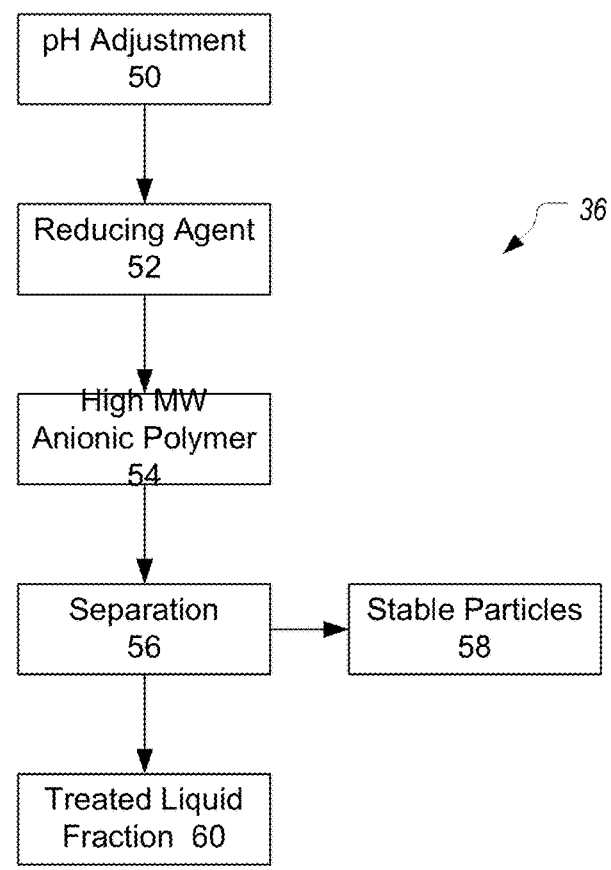
FIG. 2 illustrates methods and systems for forming stable particles from suspended solids produced during fermentation.

While the treatment step 36 can comprise any suitable steps or process, FIG. 2 shows, at least in some embodiments, that treatment step 36 comprises one or more optional steps including without limitation, a pH adjustment step 50, a reducing agent step 52, a polymer step 54, a separation step 56, a stable particles step 58, and/or a treated liquid fraction step 60. The treatment step 36 can be applied to any suitable fraction produced by ethanol fermentation. In some embodiments, the treatment step is applied to whole stillage. In other embodiments, the treatment step is applied to thin stillage. In yet other embodiments, the treatment step is applied to vinasse. In general, the treatment step can reduce the concentration of total solids and, more specifically, total suspended solids in the treated fraction by forming total suspended solids into stable particles that can be separated from the treated liquid fraction. In some embodiments, the fraction to be treated comprises greater than 5% total solids. In other embodiments, the fraction to be treated comprises greater than 9-10% total solids. In yet other embodiments, the fraction to be treated comprises greater than 14% total solids.

In some embodiments, the optional pH adjustment step 50 comprises any suitable methods, processes, and/or steps to adjust the stillage to a suitable pH for forming stabilized particles. In other embodiments, the optional pH adjustment step 50 comprises determining the pH of the stillage and then adjusting the pH to an acidic pH. In yet other embodiments, the pH is adjusted to a pH between about 2 and 6. In some embodiments, the pH is adjusted to a pH between about 3 and 6. In other embodiments, the pH is adjusted to a pH between about 3.5 and 5.5. In yet other embodiments, the pH is adjusted to a pH between about 3.8 and 5.2. In some embodiments, the pH is adjusted to between about 4.2 and 4.5. In other embodiments, the treatment step is applied to vinasse and the pH is adjusted to between about 3.5 and 7. In yet other embodiments, vinasse is adjusted to a pH between about 6 and 7. In some embodiments, vinasse is adjusted to a pH of about 6.6. In other embodiments, the pH is not adjusted because the pH of the thin stillage is already at an acceptable value.

In some embodiments, the optional reducing agent step 52 comprises any suitable methods, processes, and/or steps to add reducing agent to the fraction to be treated. In other embodiments, a reducing agent is added to the fraction. In yet other embodiments, the reducing agent includes any suitable chemical component that is suitable for electrochemically reducing the fraction.

The reducing agent is preferably classified as GRAS (generally recognized as safe) by the U.S. Food and Drug Administration. Such substances are not known to be hazardous to health. That means that recovered products may be used for human and animal consumption. In some embodiments, the reducing agent is selected to be GRAS and also selected to be compatible with the fermentation step. For example, sodium salts may inhibit proper yeast function, whereas potassium salts are compatible with yeast function. In one non-limiting embodiment, the reducing agent is potassium metabisulfite which is GRAS and also compatible with the fermentation step. Other non-limiting examples of reducing agents include sodium metabisulfite, potassium permanganate, aluminum sulfate, aluminum chloride, polyaluminum chloride, ferric chloride, ferric sulfate and ferrous sulfate.

In some embodiments, the polymer step 54 comprises any suitable methods, processes, and/or steps to add high molecular weight anionic polymer to the fraction to be treated. The polymer facilitates forming stable particles from the fraction to be treated. The polymer can include any high molecular weight anionic polymer suitable for forming stable particles. For example, the high molecular weight anionic polymer can comprise polymers with a molecular weight greater than 10 million Da. The high molecular weight anionic polymer can comprise polymers with a molecular weight greater than 15 million Da. The high molecular weight anionic polymer can comprise polymers with a molecular weight greater than 20 million Da. In some embodiments, the high molecular weight anionic polymer comprises polymers with a molecular weight between about 16 and 25 million Da. In other embodiments, the high molecular weight anionic polymer comprises polymers with a molecular weight between about 20 and 22 million Da. In general, the high molecular weight anionic polymer is selected to form stable particles and to form particles that can be separated. The high molecular weight anionic polymer can be selected to form particles that can be easily separated by mechanical separation. The high molecular weight anionic polymer can be selected to form particles that facilitate free draining. The high molecular weight anionic polymer can selected from a GRAS polymer. The high molecular weight anionic polymer can selected from a food grade polymer. The high molecular weight anionic polymer can selected from a kosher polymer.

In some embodiments, the high molecular weight anionic polymer is selected from a polyacrylamide. In other embodiments, the level of anionicity is obtained by copolymerization with acrylic acid. In yet other embodiments, the high molecular weight anionic polymer has an anionicity of at least 50 mole percent. In some embodiments, the high molecular weight anionic polymer has an anionicity of at least 60 mole percent. In some embodiments, the high molecular weight anionic polymer has an anionicity of at least 70 mole percent. In some embodiments, the high molecular weight anionic polymer has an anionicity of at least 80 mole percent. In some embodiments, the high molecular weight anionic polymer has an anionicity of at least 90 mole percent. In some embodiments, the high molecular weight anionic polymer has an anionicity of at least 95 mole percent. In other embodiments, the high molecular weight anionic polymer has an anionicity of between 50 and 100 mole percent.

High molecular weight anionic polymers can include any suitable polymers. For example, high molecular weight anionic polymer can include one or more of suitable polymers sourced from Florget (SNF, Inc., Riceboro, Ga., USA). The high molecular weight anionic polymer can include one or more of: AN 956 SH, GR, VHM (VHM=very high molecular charge); AN956 VHM with 50 mole % charge; AN 977 VHM with 70 mole % charge; and/or AN 999 VHM with 100 mole % charge.

In some embodiments, the separation step 56 comprises any suitable methods, processes, and/or steps to separate the stable particles from the treated fraction. For example, the separation step 56 can comprise one or more mechanical separation processes such as centrifugation, filtration, filter press, belt press, free draining over a screen, or any other suitable process. In other embodiments, the optional separation step comprises free draining to separate the stable particles from the recovered treated liquid fraction. In yet other embodiments, the separation step comprises free draining over a screen comprising a suitable mesh size. In some embodiments, the separation step comprises free draining over a 25 µm screen.

In some embodiments, the stable particles step 58 comprises any suitable methods, processes, and/or steps to recover the stable particles that have been separated from the treated liquid fraction. The recovered stable particles can be recovered by one or more of being scrapped from a filter screen, being recovered from a centrifuge, being recovered from a filter press, and/or being recovered from a belt press. In some embodiments, the recovered stable particles are added to the wet grains for further processing. In other embodiments, the recovered stable particles are added to the dried grains. In yet other embodiments, the recovered stable particles are further processed to result in useful products such as livestock feed and/or food additives. In some embodiments, the recovered stable particles are classified as GRAS. In some embodiments, the recovered stable particles are used as feed for livestock including cattle, chickens, pigs and other similar animals.

In some embodiments, the treated liquid fraction (sometimes referred to herein as "clarified thin stillage") step 60 can comprise any suitable methods, processes, and/or steps to recover the treated liquid fraction (clarified thin stillage) and/or to recycle the treated liquid (sometimes referred to herein as "clarified backset") fraction. In other embodiments, the treated liquid fraction (clarified thin stillage) is recovered from the separation step and recycled to the fermentation (cook) step as "clarified backset," labeled as step 37 in FIG. 1. The treated liquid fraction (clarified backset) can be added to the fermentation (cook) step along with other water sources which can be, but are not limited to: fresh water, $CO_2$ scrubber make up, evaporation condensate. In some embodiments, the treated liquid fraction 60 ("clarified backset") can be added to the fermentation (cook) step at an amount ranging from 0% by volume of the total input liquid (in the case of potable alcohol preparation) to about 90% by volume of the total input liquid. The treated liquid fraction 60 can be added to the fermentation step along with fresh input liquid. In some embodiments, the treated liquid fraction can be added to the fermentation step at an amount ranging from about 0% to about 90% by volume of the total input liquid. In other embodiments, the treated liquid fraction can be added to the fermentation step at an amount of up to 85% by volume of the total input liquid. In yet other embodiments, the treated liquid fraction can be added to the fermentation step at an amount of between about 20% to about 85% by volume of the total input liquid. For example the treated liquid fraction can be added to the fermentation step at an amount of more than about 0%, 20%, 30%, 40%, 50%, 60%, 70%, 80%, or 90% by volume of the total input liquid. In some embodiments, the TS and TSS recovered from the treated liquid fraction ("clarified thin stillage") are further processed to yield valuable commodities such as proteins and oils.

In some embodiments, the treated liquid fraction ("clarified thin stillage") comprises a removal of more than 50% by weight of TSS. In other embodiments, the treated liquid fraction comprises a removal of more than 75% by weight of TSS. In yet other embodiments, the treated liquid fraction comprises a removal of more than 80% by weight of TSS. In some embodiments, the treated liquid fraction comprises a removal of more than 90% by weight of TSS. In other embodiments, the treated liquid fraction comprises a removal of more than 95% by weight of TSS. In yet other embodiments, the treated liquid fraction comprises a removal of more than 98% by weight of TSS. In some embodiments, the treated liquid fraction comprises a removal of more than 25% by weight of TS. In other embodiments, the treated liquid fraction comprises a removal of more than 35% by weight of TS. In yet other embodiments, the treated liquid fraction comprises a removal of more than 50% by weight of TS. In some embodiments, the treated liquid fraction is classified as GRAS.

This application discloses a number of methods and systems for forming stabilized particles from solids and/or suspended solids produced by ethanol fermentation. The application discloses a number of advantages including, without limitation:

Treatment of thin stillage, thick stillage, or vinasse with reducing agents and high molecular weight (>15,000,000 Da) anionic polymers under acidic conditions can result in a greater than 98% removal of TSS and a greater than 50% removal of TS.

The reducing agents can include any suitable reducing agents in any suitable combination and can include metals, bisulfites, and their respective salts.

The combination of reducing agent and high molecular weight (HMW) anionic polymer can result in excellent recovery of proteins, yeasts, and oils than using polymer alone.

Biologically active compounds such as intact proteins and yeast can be recovered without heat, vacuum, or pressure damage that can occur in conventional post fermentation processing, such as conventional evaporation processes.

The oils/fatty acids recovered have a lower rancidity values and higher omega 3, 6, 9 values compared to oils recovered using conventional evaporation process to concentrate the oils.

Each of the reducing agents and high molecular weight anionic polymers can be selected from compounds classified as generally recognized as safe (GRAS). Using reducing agents and high molecular weight anionic polymers selected from compounds classified as GRAS can allow for the treated solids and/or recovered liquid fraction to be used as livestock feed and/or in products for human consumption.

The treatment can be carried out under a range of acidic conditions from about pH 3.5 to 5.5. This pH range can approximate the initial pH range of the stillage. Therefore, in some instances, no major changes in pH are required.

Treatment of stillage can allow for free drainage of stabilized particles at any total solids level.

Treatment of stillage can allow for free drainage of stabilized particles at any total suspended solids level.

Treatment can allow for improved recycling of the treated liquid fraction ("clarified backset") as backset. The disclosed treatment can allow for up to 90% by volume of the treated liquid fraction ("clarified backset") to be recycled as backset. This dramatic increase in the ability to recycle the liquid fraction can eliminate the need for expensive evaporation processes otherwise required to treat the unrecyclable thin stillage and can improve the overall water balance of the ethanol production facility.

The treated and recovered stable particle solids can be added to DDG to increase the nutritional value of DDG.

The disclosed treatment process can be effective in treating stillage produced from a wide variety of feedstocks. The disclosed treatment process can be effective for treating stillage produced from a single feedstock source such as corn, sugar cane, agave or other similar feedstocks. The disclosed treatment process can also effective for treating stillage produced from blends of feedstocks such as blends of corn, barley, rye, oats, wheat, and other similar feedstock blends. The disclosed treatment process can be effective in treating vinasse such as agave vinasse and other vinasses. The disclosed treatment process can be effective in treating stillage produced from ethanol plants configured to ferment C-6 sugars and from ethanol plants configured to ferment C-5 sugars (hemicellulose facilities).

The disclosed treatment process can recover fatty acids from the stillage for further processing without damaging the fatty acids. In some instances, there is no change in the composition of the recovered fatty acids and there is no loss in recovery of the fatty acids.

There is a distinction between an industrial or fuel ethanol process and a potable ethanol process in how treated and clarified thin stillage can be used. Potable ethanol processes generally will not return the clarified thin stillage as backset to the fermentation process. In all cases potable ethanol processes will recycle a fraction of the untreated thin stillage back to fermentation process and the rest of the thin stillage will be processed in some manner and disposed of. Potable alcohol producers are worried about producing desired flavors and not about recycling water. In contrast, an industrial or fuel ethanol plant is concerned about efficient recycling of water. For this reason, the clarified thin stillage may be recycled at an amount ranging from 0% by volume up to 90% by volume of the total input liquid. The only reason the percentage is not greater than 90% is that there will always be some fresh water added in industrial or fuel ethanol plants as water that passes through the $CO_2$ scrubber to collect up ethanol vapors from the fermentation tanks, which is then added to the initial fermentation (cook) water.

Example 1

A study was carried out in which thin stillage was treated as described above. Aluminum chlorohydrate was added as the reducing agent. The addition of aluminum chlorohydrate as the reducing agent generated stabilized particles and allowed for the stabilized particles to be separated on filter screens. Other metals were also employed as reducing agents and similar stabilized particles were generated. Sodium metabisulfite ($Na_2S_2O_5$) was also used as a reducing agent and was found to be effective. The use of a reducing agent stabilized the formed particles and allowed for exceptional removal of TSS, partial removal of TS, and almost a complete removal of yeasts. As described above, the study was carried out by adjusting pH of the thin stillage, adding a reducing agent, adding a high molecular weight anionic polymer, and separating the stabilized particles from the recovered liquid fraction.

In the study it was discovered that in the absence of reducing agent, that the formed particle became less stable and susceptible to fragmentation when the concentration of total solids was greater than 10-13%. It was also noticed that adding a reducing agent improved free drainage and seemed to stabilize the formed particles. A test run of thin stillage with a 7-9% solids concentration that was treated with reducing agent and high molecular weight anionic polymer resulted in free drainage on a 25 micron screen. In contrast, a control run with a 7-9% solid concentration without reducing agent resulted in slow drainage and buildup of particles on the screen. This required scraping of the screen to allow for drainage. It also required continuous washing cycle of screen to achieve the original level of drainage seen in the test run. Another test run with a greater than 12% solids concentration that was treated with reducing agent and high molecular weight anionic polymer resulted in free drainage on a 25 micron screen.

Example 2

A study was carried out on thin stillage obtained from Brown Forman distilleries in Kentucky, USA. The thin stillage was treated as described above, with the exception that a reducing agent was not utilized. The recovered solids were analyzed as wet solids and on a dry weight basis. Thin stillage was also evaporated by conventional evaporation techniques to produce evaporated syrup that was used as a comparison for the treated thin stillage. The recovered solids were determined to have an overall moisture content of about 83.26% and a dry matter content of about 16.74%. The recovered solids were analyzed for crude protein, fat, fiber, and other components. The results for crude protein, fat, fiber, and other components are listed below in Table 1. The recovered solids were also analyzed for amino acid content. The results for the amino acid analysis are listed below in Table 2.

TABLE 1

| Test Performed | Wet Solids | Dry Weight Basis |
|---|---|---|
| Moisture (%) | 83.26 | — |
| Dry Matter (%) | 16.74 | — |
| Ash (%) | 0.55 | 3.26 |
| Crude Protein (%) | 5.42 | 32.39 |
| Crude Fat (%) | 1.55 | 9.25 |
| Crude Fiber (%) | 1.21 | 7.23 |
| Acid Detergent Fiber (%) | 1.69 | 10.07 |
| Neutral Detergent Fiber (%) | 5.39 | 32.19 |
| Calcium (ppm) | 74 | 439 |
| Copper (ppm) | 3.4 | 20 |
| Iron (ppm) | 66 | 393 |
| Magnesium (ppm) | 200 | 1192 |
| Manganese (ppm) | 3.3 | 20 |
| Phosphorus (ppm) | 1183 | 7065 |
| Potassium (ppm) | 683 | 4078 |
| Sodium (ppm) | 44 | 263 |
| Total Available Starch (%) (Washed) | 2.84 | 16.95 |
| Sulfur (%) | 543 | 0.32 |
| Zinc (ppm) | 21 | 125 |
| Nitrogen Conversion (%) | 0.87 | 5.18 |
| Total Starch (%) | 1.52 | 9.09 |
| Yeast & Mold (cfu/g) | 94000 | |

TABLE 2

| Test Performed | Wet Solids | Dry Weight Basis |
|---|---|---|
| Moisture (%) | 83.26 | — |
| Dry Matter (%) | 16.74 | — |
| Alanine (%) | 0.33 | 1.96 |
| Arginine (%) | 0.24 | 1.46 |
| Aspartic Acid (%) | 0.47 | 2.79 |
| Cystine (%) | 0.08 | 0.49 |
| Glutamic Acid (%) | 0.84 | 4.99 |
| Glycine (%) | 0.23 | 1.38 |
| Histadine (%) | 0.13 | 0.81 |
| Isoleucine (%) | 0.23 | 1.36 |
| Leucine (%) | 0.48 | 2.86 |
| Lysine (%) | 0.27 | 1.59 |
| Methionine (%) | 0.70 | 4.15 |
| Phenylalanine (%) | 0.26 | 1.57 |
| Proline (%) | 0.36 | 2.13 |
| Serine (%) | 0.29 | 1.74 |
| Threonine (%) | 0.25 | 1.50 |
| Tyrosine (%) | 0.13 | 0.77 |
| Tryptophan (%) | 0.06 | 0.37 |
| Valine (%) | 0.29 | 1.74 |

The yeast from the treated stillage were found to be intact and biologically active. This is in contrast to the yeast in stillage that has been passed through an evaporator. Yeast that are processed in an evaporator are often destructed or partially destructed. The percentage of crude protein and crude fat were higher than normally found in evaporator processed thin stillage. Conventional evaporative processes can be very energy intensive. The evaporative processes often involve high temperature (160-230° F.), vacuum under 2 bar, and/or under pressures above 25 PSI, and/or 30 minutes of more of retention time from influent to effluent with often greater than 90% recovery of solids. Waste heat generated in evaporation can be used to drive the distillation columns. In some cases, the results show that the disclosed process can eliminate or minimize the need for evaporators.

Further amino acid analysis was performed on evaporated syrup produced by conventional evaporation and on the treated stillage. Table 3 below shows the further amino acid analysis that was performed.

TABLE 3

| Amino Acid | Conventional evaporated syrup | Solids from treated stillage | Conventional evaporated syrup, dry basis | Solids from treated stillage, dry basis | Difference treated to conventional (%) | Spent yeast, dry basis | Aventine, distillers yeast |
|---|---|---|---|---|---|---|---|
| Tryptophan | 0.05% | 0.07% | 0.15% | 0.29% | 89.6% | 0.37% | 1.20% |
| Cystine | 0.07% | 0.09% | 0.22% | 0.38% | 74.1% | 0.49% | 1.30% |
| Methionine | 0.09% | 0.12% | 0.28% | 0.50% | 80.6% | 4.15% | 1.70% |
| Aspartic | 0.39% | 0.44% | 1.20% | 1.83% | 52.8% | 2.79% | 8.60% |
| Threonine | 0.20% | 0.24% | 0.62% | 1.00% | 62.5% | 1.50% | 4.40% |
| Serine | 0.23% | 0.30% | 0.71% | 1.25% | 76.6% | 1.74% | 4.10% |
| Glutamic | 0.83% | 0.94% | 2.55% | 3.92% | 53.4% | 4.99% | 11.10% |
| Proline | 0.30% | 0.38% | 0.92% | 1.58% | 71.5% | 2.13% | 4.90% |
| Glycine | 0.29% | 0.29% | 0.89% | 1.21% | 35.4% | 1.38% | 4.40% |
| Alanine | 0.36% | 0.44% | 1.11% | 1.83% | 65.5% | 1.96% | 6.60% |
| Valine | 0.24% | 0.34% | 0.74% | 1.42% | 91.8% | 1.74% | 5.80% |
| Isoleucine | 0.15% | 0.23% | 0.46% | 0.96% | 107.6% | 1.36% | 4.50% |
| Leucine | 0.32% | 0.58% | 0.98% | 2.42% | 145.4% | 2.86% | 8.50% |

TABLE 3-continued

| Amino Acid | Conventional evaporated syrup | Solids from treated stillage | Conventional evaporated syrup, dry basis | Solids from treated stillage, dry basis | Difference treated to conventional (%) | Spent yeast, dry basis | Aventine, distillers yeast |
|---|---|---|---|---|---|---|---|
| Tyrosine | 0.14% | 0.25% | 0.43% | 1.04% | 141.8% | 0.77% | 3.70% |
| Phenylalanine | 0.16% | 0.30% | 0.49% | 1.25% | 153.9% | 1.57% | 4.40% |
| Total Lysine | 0.28% | 0.27% | 0.86% | 1.13% | 30.6% | 1.59% | 6.40% |
| Histidine | 0.13% | 0.17% | 0.40% | 0.71% | 77.1% | 0.81% | 2.30% |

A fatty acid profile analysis was also carried out on evaporated syrup produced by conventional evaporation and on the treated stillage. Table 4 below shows the fatty acid profile analysis.

TABLE 4

| Fatty Acid | Conventional evaporated syrup | Solids from treated stillage | Conventional evaporated syrup, dry basis | Solids from treated stillage, dry basis | Difference treated to conventional (%) |
|---|---|---|---|---|---|
| C08:0-C24:1 Total Fatty Acid | 5.93% | 10.52% | 18.25% | 43.83% | 140.2% |
| C08:0 Octanoic (Caprylic) | 0.01% | 0.01% | 0.03% | 0.04% | 35.4% |
| C10:0 Decanoic (Capric) | 0.01% | 0.01% | 0.03% | 0.04% | 35.4% |
| C11:0 Undecanoic (Hendecanoic) | 0.01% | 0.01% | 0.03% | 0.04% | 35.4% |
| C12:0 Dodecanoic (Lauric) | 0.01% | 0.01% | 0.03% | 0.04% | 35.4% |
| C14:0 Tetradecanoic (Myristic) | 0.01% | 0.01% | 0.03% | 0.04% | 35.4% |
| C14:1 Tetradecenoic acid | 0.01% | 0.01% | 0.03% | 0.04% | 35.4% |
| C15:1 Pentadecanoic | 0.01% | 0.01% | 0.03% | 0.04% | 35.4% |
| C16:0 Hexadecanoic (Palmitic) | 0.86% | 1.52% | 2.65% | 6.33% | 139.3% |
| C16:1 Hexadecenoic (Palmitoleic) | 0.02% | 0.03% | 0.06% | 0.13% | 103.1% |
| C17:0 Heptadecanoic (Margaric) | 0.01% | 0.01% | 0.03% | 0.04% | 35.4% |
| C17:1 Heptadecenoic (Margaroleic) | 0.01% | 0.01% | 0.03% | 0.04% | 35.4% |
| C18:1 Octadecanoic (Stearic) | 0.13% | 0.21% | 0.40% | 0.88% | 118.8% |
| C18:1 Octadecenoic (Oleic) | 1.74% | 3.12% | 5.35% | 13.00% | 142.8% |
| C18:2 Octadecadienoic (Linoleic) | 3.00% | 5.31% | 9.23% | 22.13% | 139.7% |
| C18:3 Octadecatrienoic (Linolenic) | 0.09% | 0.17% | 0.28% | 0.71% | 155.8% |
| C18:4 Octadecatetraenoic | 0.01% | 0.01% | 0.03% | 0.04% | 35.4% |
| C20:0 Eicosanoic (Arachidic) | 0.02% | 0.04% | 0.06% | 0.17% | 170.8% |
| C20:1 Eicosenoic (Gadoleic) | 0.02% | 0.03% | 0.06% | 0.13% | 103.1% |
| C20:2 Eicosadienoic | 0.01% | 0.01% | 0.03% | 0.04% | 35.4% |
| C20:3 Eicosatrienoic | 0.01% | 0.01% | 0.03% | 0.04% | 35.4% |
| C20:4 Eicosatetraenoic (Arachidonic) | 0.01% | 0.01% | 0.03% | 0.04% | 35.4% |
| C20:5 Eicosapentaenoic | 0.01% | 0.01% | 0.03% | 0.04% | 35.4% |
| C21:5 Heneicosapentaenoic | 0.01% | 0.01% | 0.03% | 0.04% | 35.4% |
| C22:0 Docosanoic (Behenic) | 0.01% | 0.02% | 0.03% | 0.08% | 170.8% |
| C22:1 Docosenioc (Erucic) | 0.01% | 0.01% | 0.03% | 0.04% | 35.4% |
| C22:2 Docosadienoic | 0.01% | 0.01% | 0.03% | 0.04% | 35.4% |
| C22:3 Docosatrienoic | 0.01% | 0.01% | 0.03% | 0.04% | 35.4% |
| C22:4 Docosatetraenoic | 0.01% | 0.01% | 0.03% | 0.04% | 35.4% |
| C22:5 Docosapentaenoic | 0.01% | 0.01% | 0.03% | 0.04% | 35.4% |
| C22:6 Docosahexaenoic | 0.01% | 0.01% | 0.03% | 0.04% | 35.4% |
| C24:0 Tetracosanoic (Lignoceric) | 0.02% | 0.03% | 0.06% | 0.13% | 103.1% |
| C24:1 Tetracosenioc (Nervonic) | 0.01% | 0.01% | 0.03% | 0.04% | 35.4% |
| C08:0-C24:1 Total Fatty Acid | 5.93% | 10.52% | 18.25% | 43.83% | 140.2% |
| Total Fatty Acids | 5.93% | 10.52% | 18.25% | 43.83% | 140.2% |

The study results were analyzed and revealed that treatment with high molecular weight anionic polymer results in comparable amino acid and fatty acid profiles when compared to evaporated syrup produced by conventional evaporation.

Example 3

Fermentation waste from an ethanol production plant was treated according to the methods and systems described above. Table 5 lists test results for raw effluent from the fermentation process. Table 6 lists test results for effluent treated as described above with potassium metabisulfite used as the reducing agent.

TABLE 5

| Test Performed: | Results: | Testing Method: |
| --- | --- | --- |
| Biochemical Oxygen | 60,000 mg/L | SM 5210 B |
| Chemical Oxygen Demand | 113,000 mg/L | EPA 410.4 |
| Sulfite | 100 mg/L | EPA 377.1 |
| Sulfate, SO4 | 139 mg/L | EPA 300.0 |
| Total Suspended Solids (TSS) | 26,000 mg/L | SM 2540 D |
| Residue, Total, TS | 67,000 mg/L | SM 2540 D |

TABLE 6

| Test Performed: | Results: | Testing Method: |
| --- | --- | --- |
| Biochemical Oxygen | 37,000 mg/L | SM 5210 B |
| Chemical Oxygen Demand | 74,100 mg/L | EPA 410.4 |
| Sulfite | 200 mg/L | EPA 377.1 |
| Sulfate, SO4 | 214 mg/L | EPA 300.0 |
| Total Suspended Solids (TSS) | <3 mg/L | SM 2540 D |
| Residue, Total, TS | 54,600 mg/L | SM 2540 D |

The test results indicated a substantial reduction in TSS from 26,000 mg/L to less than 3 mg/L. The test results also indicated a reduction in TS from 67,000 mg/L to 54,600 mg/L.

Example 4

Fermentation waste from an ethanol production plant was treated according to the methods and systems described above. The samples were treated with potassium metabisulfite with 15-20 minutes of mixing and with a 50 mole percent anionic polyacrylamide.

Samples were then sent to an analytical laboratory to analyze the TS, TSS, and fatty acid content. Table 7 lists test results for syrup solid derived from thin stillage prepared by conventional means. Table 8 lists test results for whole stillage treated with potassium metabisulfite and HMW anionic polymer. Table 9 lists test results for thin stillage treated with potassium metabisulfite and HMW anionic polymer.

TABLE 7

| Test Performed: | Results: |
| --- | --- |
| Total Solids (TS) | 25.80% |
| Total Suspended Solids (TSS) | 18.35% |
| Total Fatty Acids | 13.56% |

TABLE 8

| Test Performed: | Results: |
| --- | --- |
| Total Solids (TS) | 7.35% |
| Total Suspended Solids (TSS) | 2.07% |
| Total Fatty Acids | 1.47% |

TABLE 9

| Test Performed: | Results: |
| --- | --- |
| Total Solids (TS) | 5.28% |
| Total Suspended Solids (TSS) | 0.04% |
| Total Fatty Acids | 0.01% |

Figure 3:
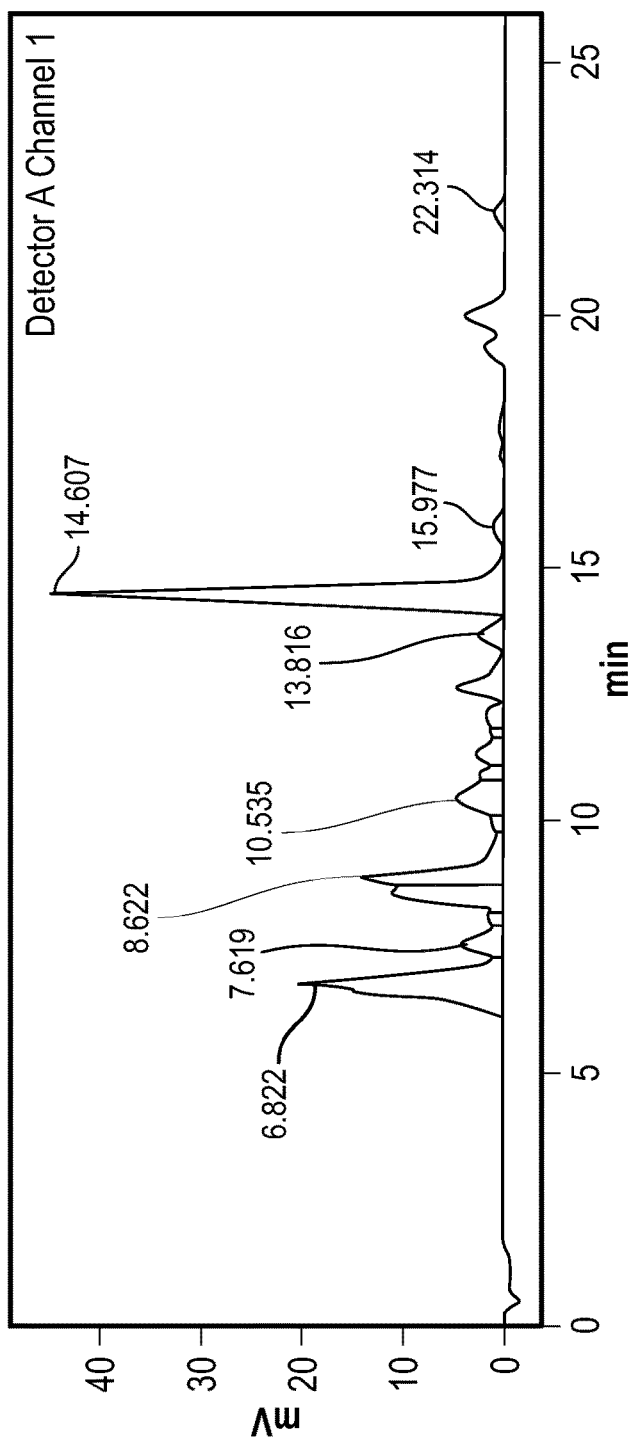
FIG. 3 illustrates an HPLC analysis of a sample before treatment to form stable particles.
Figure 4:
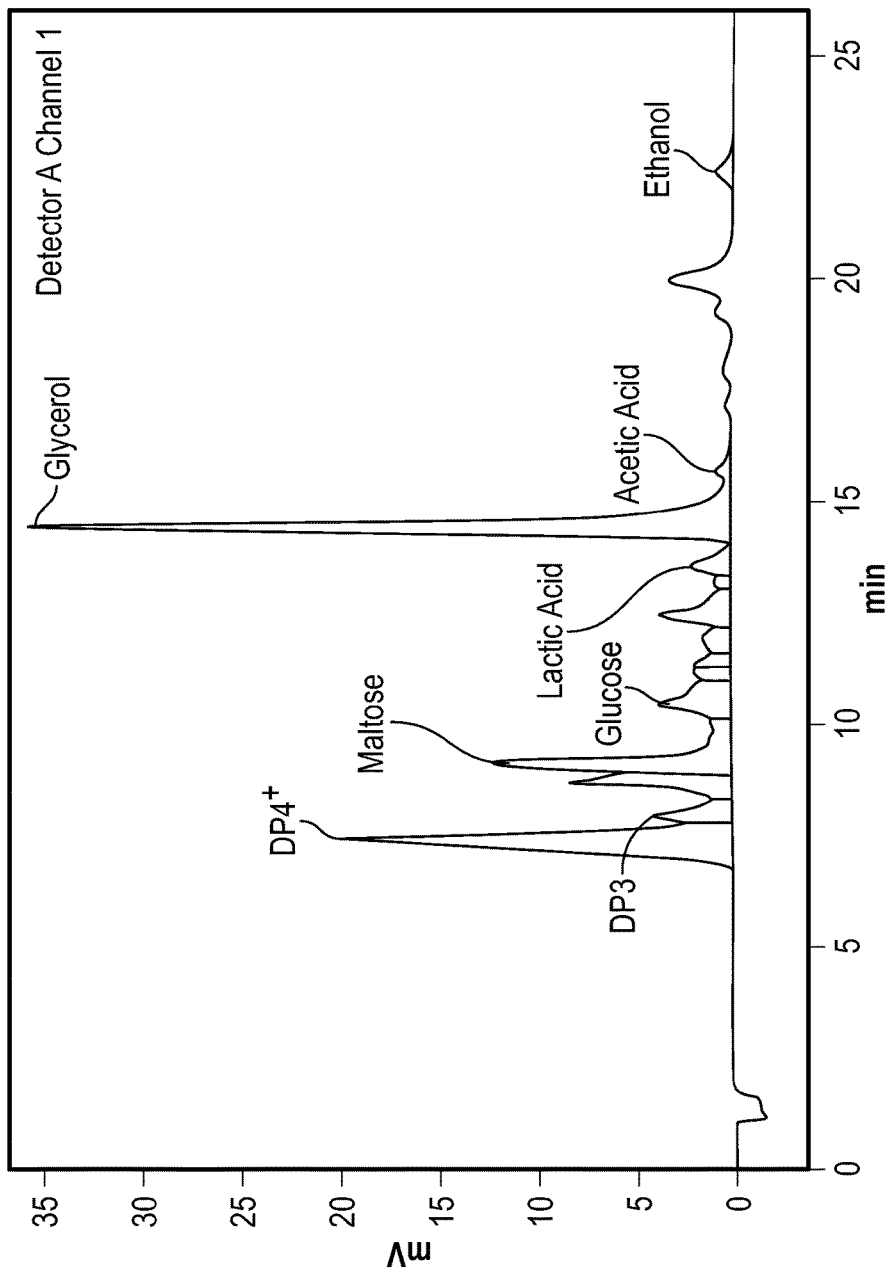
FIG. 4 illustrates an HPLC analysis of a sample after treatment to form stable particles.

Samples from treated whole stillage and treated thin stillage were then analyzed by HPLC to further characterize the samples. FIG. 3 shows the HPLC results for treated whole stillage. FIG. 4 shows the HPLC results for treated thin stillage. There was a notable reduction in acetic acid which may indicate the separation of fatty acids from the whole stillage.

The terms "a," "an," "the" and similar referents used in the context of this application (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the application and does not pose a limitation on the scope of the application otherwise claimed. No language in the specification should be construed as indicating any non-claimed element essential to the practice of the disclosure.

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

Groupings of alternative elements or embodiments of the application disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this application are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the application to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

It is to be understood that the embodiments of the application disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention claimed is:

1. A method for forming stable particles from suspended solids produced by ethanol fermentation, the method comprising:
    providing a liquid fraction from ethanol fermentation, the liquid fraction comprising one or more of solids and suspended solids, wherein the liquid comprises thin stillage;
    adjusting a pH of the liquid fraction to a pH in the range from 3.5 to 7;
    adding a potassium metabisulfite reducing agent to the pH adjusted liquid fraction;
    adding a high molecular weight anionic polymer to form stable particles of one or more of solids and suspended solids, wherein the high molecular weight anionic polymer comprises a molecular weight of about 15 million Da or more; and
    free draining to separate the stable particles from a liquid portion.

2. The method of claim 1, wherein the pH is between about 3.8 and 5.2.

3. The method of claim 1, wherein the high molecular weight anionic polymer comprises a molecular weight of about 16 to 25 million Da.

4. The method of claim 1, wherein the high molecular weight anionic polymer comprises a molecular weight of about 20 to 22 million Da.

5. The method of claim 1, wherein the liquid portion comprises removal of more than 75% by weight of total suspended solids (TSS) compared to the fraction from ethanol fermentation.

6. The method of claim 1, wherein the liquid portion comprises removal of more than 90% by weight of total suspended solids (TSS) compared to the fraction from ethanol fermentation.

7. The method of claim 1, wherein the liquid portion comprises removal of more than 95% by weight of total suspended solids (TSS) compared to the fraction from ethanol fermentation.

8. A method for increasing a ratio of backset to input liquid for a fermentation process, the method comprising:
    preparing a fermentation liquid fraction from a fermentation process, the fermentation liquid fraction comprising solids and suspended solids, wherein the fermentation liquid fraction comprises thin stillage;
    adjusting a pH of the fermentation liquid fraction to a pH in the range from 3.5 to 7;
    treating the fermentation liquid fraction with a potassium metabisulfite reducing agent;
    treating the fermentation liquid fraction with a high molecular weight anionic polymer to form stable particles and a treated liquid fraction, wherein the high molecular weight anionic polymer comprises a molecular weight of about 15 million Da or more;
    separating the stable particles from the treated liquid fraction; and
    recycling the treated liquid fraction to the fermentation process as backset,
    wherein the ratio of treated liquid fraction used as backset exceeds 20% of a total input of liquid into the fermentation process.

9. The method of claim 8, wherein the pH is between about 3.8 and 5.2.

10. The method of claim 8, wherein the high molecular weight anionic polymer comprises a molecular weight of about 16 to 25 million Da.

11. The method of claim 8, wherein the high molecular weight anionic polymer comprises a molecular weight of about 20 to 22 million Da.

12. The method of claim 8, wherein the ratio of treated liquid fraction used as backset exceeds 30% of a total input of liquid into the fermentation process.

13. The method of claim 8, wherein the ratio of treated liquid fraction used as backset exceeds 40% of a total input of liquid into the fermentation process.

* * * * *